US005688647A

United States Patent [19]
Griffiths

[11] Patent Number: 5,688,647
[45] Date of Patent: Nov. 18, 1997

[54] DETECTION OF DINUCLEOTIDE REPEAT POLYMORPHISM IN EXON 18 OF LDL RECEPTOR GENE FOR DETERMINING PREDISPOSITION TO OBESITY

[75] Inventor: Lynette Robyn Griffiths, Burleigh Heads, Australia

[73] Assignee: Griffith University, Queensland, Australia

[21] Appl. No.: 569,872

[22] Filed: Dec. 8, 1995

[51] Int. Cl.$^6$ .............................. C12Q 1/68; C12P 19/34
[52] U.S. Cl. .................................... 435/6; 435/912
[58] Field of Search ........................ 435/6, 91.2

[56] References Cited

PUBLICATIONS

Griffiths et al., Clin. Exp. Pharm. Physiol. 22, 496–498 (Jun.–Jul. 1995).
Zee et al., Clin. Genet. 47(3), 118–121 (1995).
Morris et al., Clin. Sci. 86, 583–592 (1994).
Zee et al., Biochem. Biophys. Res. Comm. 189(2), 965–971 (1992).
Zuliani et al., Nucleic Acids Res. 18(14), 4300 (1990).
Genetic Aspects of Susceptibility to Obesity and Related Dyslipidemias, Despres, et al., Molecular and Cellular Biochemistry, 113: 151–169, 1992.
Does Obesity Run in Families Because of Genes?, Serense, et al., Acta Psychiatrica Scandinavica, 370: 67–72, 1993.
Multiple Metabolic Syndrome: Aspects of Genetic Epidemiology and Molecular Genetics, Kesaniemi, et al., Annals of Medicine, 24: 461–464, 1992.
The LDL Receptor Gene: A Mosaic of Exons Shared with Different Proteins, Sudhof, et al., Science, 228, 815–822, 1985.
Linkage of atherogenic Lipoprotein Phenotype to the Low Density Lipoprotein Receptor Locus on the Short Arm of Chromosome 19, Nishina, et al., Procceeding of the National Academy of Science U.S.A., 89: 708–712, 1992.
Significant Relationships of Plasma Lipids and Body Mass Index with Polymorphism at the Linked Low–Density–Lipoprotein Receptor Gene and Insulin Receptor Gene Loci (19;13.2) in Essential Hypertensive Patients, Morris, et al., Clinical Science, 228: 815–822, 1985.
Marked Association of a Relp for the Low Density Lipoprotein Receptor Gene with Obesity in Essential Hypertensives, Lee, et al., Biochemical Biophysical Research Communications, 189; 965–971, 1992.
Association of HincII RFLP of Low Density Lipoprotein Receptor Gene with Obesity in Essential Hypertensives, Lee, et al., Clinical Genetics, 147: 118–121, 1995.
Dinucleotide Repeat Polymorphism at the 3'End of the LDL Receptor Gene, Zuliani, et al., Nucleic Acid Research, 18, 4300, 1990.
Cross–Sectional Study of a Microsatellite Marker in the Low Density Lipoprotein Receptor Gene in Obese Normotensives, Griffiths, et al., Proccdings of the HBPRCA, 1995.

Primary Examiner—Kenneth R. Horlick
Attorney, Agent, or Firm—Knobbe, Martens, Olson & Bear, LLP

[57] ABSTRACT

A method detects whether an individual is predisposed to obesity. The method includes the steps of (i) obtaining a sample containing human genomic DNA from the individual; (ii) detecting whether the genomic DNA in the sample has a 7 AT tandem repeat in exon 18 of the low density lipoprotein receptor gene on one or both chromosomes; and (iii) correlating the absence of the 7 AT tandem repeat on the chromosome or chromosomes with a predisposition to obesity in the individual.

5 Claims, 5 Drawing Sheets

GZ-7 = CACTTTGTATATTGGTTGAAACTGT

GZ-8 = CACTGAACAAAATAGAGCAACCAGGG

FIG. 1

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

CACTTTGTAT ATTGGTTGAA ACTGT 25

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

CACTGAACAA ATACAGCAAC CAGGG 25

DETECTION OF DINUCLEOTIDE REPEAT POLYMORPHISM IN EXON 18 OF LDL RECEPTOR GENE FOR DETERMINING PREDISPOSITION TO OBESITY

BACKGROUND OF THE INVENTION

1. Technical Field

This invention relates to a method for detecting individuals who are predisposed to obesity. This invention further relates to genetic techniques for detecting a low density lipoprotein receptor gene (LDLR) microsatellite polymorphism.

2. Background

Obesity is a common nutritional disorder that affects approximately 30% of adults in the Western world. Obesity is a multifactorial condition in which both environmental and genetic factors are important determinants in susceptibility to body fat accumulation (Despres et al., 1992, *Molecular and Cellular Biochemistry*, 113, 151–169). Adoption studies have implicated genetic control, rather than childhood environment, as the main influence on the development of adult obesity (Sorensen, T. I. & Stunkard, A. J., 1993, *Acta Psychiatrica Scandinavica*, 370, 67–72). Obesity, essential hypertension, impaired glucose tolerance, non-insulin-dependent diabetes mellitus and dyslipidaemia tend to cluster in families. Collectively, these abnormalities constitute the multiple metabolic syndrome or Syndrome X, which is associated with cardiovascular disease (Kesaniemi et. al., 1992, *Annals of Medicine* (Helsinki), 24, 461–464).

Lipids and cholesterol ingested in an individuals' diet are essential for body maintenance. These molecules are transported through the body in lipoproteins. There are four types of lipoproteins each responsible for transporting varying amounts of lipid and cholesterol. It has been shown that lipoprotein concentration in the blood is proportional to abdominal fat disposition in obese individuals (Nishina et al., 1992, *Proceeding of the National Academy of Science U.S.A.*, 89, 708–712). The low density lipoprotein (LDL) receptor is responsible for regulating LDL levels and hence cholesterol and plasma lipids in the blood. The gene encoding the LDL receptor (LDLR) is located at chromosome 19 position p13.2.

LDLR is approximately 45 kb in length and contains 18 exons (Südhof et al., 1985, *Science*, 228, 815–822). The ApaLI LDLR polymorphism detects a nucleotide substitution in intron 15 of this gene.

Studies of the ApaLI restriction fragment length polymorphism (RFLP) of LDLR showed an association with obesity in essential hypertensives. However, no association was shown between the ApaLI RFLP and hypertension (Zee et al., 1992, *Biochemical Biophysical Research Communications*, 189, 965–971). In a further study with a population of 70 normotensives, the ApaLI polymorphism did not show a significant association with obesity (Morris et al., 1994, *Clinical Science*, 86, 583–592). Similarly, a HincII LDLR polymorphism which detects a substitution in exon 12 showed a significant association with obesity in essential hypertensives but not in normotensives (Zee et al., 1995, *Clinical Genetics*, 47, 118–121). Both of these polymorphisms are located towards the 5' end of the gene.

There appears to be no reports associating obesity in normotensives with the LDLR gene. Furthermore, there is no known test of identifying such individuals who may be predisposed to obesity. If these individuals were aware that they were predisposed to obesity, they could be treated or follow dietary programs to prevent the onset of an obesity problem or treat an existing obesity problem.

SUMMARY OF THE INVENTION

The present invention results from the surprising discovery that a LDLR microsatellite marker located towards the 3' end of the gene showed a significant association with obesity in a mixed population of lean and obese individuals. The LDLR microsatellite marker is located in exon 18 and is a dinucleotide AT tandem repeat region. Individuals who had an AT tandem repeat number of 7 in exon 18 of the LDLE gene on both chromosomes had a statistical predisposition to being lean. Hence, individuals who did not have an AT tandem repeat of 7 in exon 18 of the LDLR gene on one chromosome had a statistical predisposition to obesity.

Thus, it is an object of the present invention to provide a method for detecting whether an individual may be predisposed to obesity. Further, individuals who had a tandem repeat of 8 or 10 in exon 18 of the LDLR gene On one chromosome and a tandem repeat of 8 or 10 in exon 18 of the LDLR gene on the other chromosome had a statistical predisposition to obesity.

In one aspect, the invention resides in a method for detecting whether an individual is disposed to obesity including the steps of:

(i) obtaining a sample containing human genomic DNA from said individual; and (ii) detecting whether said genomic DNA in said sample has a 7 AT tandem repeat in exon 18 of the low density lipoprotein receptor gene on one or both chromosomes, wherein the absence of the 7 AT tandem repeat indicates said individual is predisposed to obesity, lean being defined as having a body mass index less than 26 kg/m$^2$ and obese being defined as having a body mass index equal to or greater than 26 kg/m$^2$.

The presence of the 7 AT tandem repeat in exon 18 of the LDLR gene indicates said individual is predisposed to being lean.

The sample may be any suitable tissue or body fluid. These samples are preferably blood containing leukocyte(s).

The detecting of the AT tandem repeats preferably involves PCR amplification using suitable primers. The choice of primers will determine the size of the PCR product and hence the manner of distinguishing and identifying products. Preferably the primers disclosed in Zuliani and Hobbs et al., 1990, *Nucleic Acids Research*, 18, 4300 are used. These primers are also shown in FIG. 1. After PCR amplification the amplified products may be determined by sequence analysis or by size separation. Size separation is preferably achieved by electrophoresis of the PCR products in a suitable agarose or polyacylamide gel.

The number of tandem repeats in exon 18 of the LDLR gene may vary. Where an individual has a genotype with 7 tandem repeats in the LDLR gene on both chromosomes, or 7 tandem repeats in the LDLR gene on one chromosome and 8 or 10 tandem repeats in the LDLR gene on the other chromosome, then the individual has a predisposition to being lean. Where an individual has a genotype with 8 tandem repeats in the LDLR gene on both chromosomes, 10 tandem repeats in the LDLR gene on both chromosomes, or 8 tandem repeats in the LDLR gene on one chromosome and 10 tandem repeats in the LDLR gene on the other chromosome, then the individual has a predisposition to obesity.

In summary, the following results of the method can be achieved:

(i) 7/7 (AT tandem repeat number in exon of the LDLR gene on one chromosome/AT tandem repeat number in exon 18 of the LDLR gene on the other chromosome) indicates the individual is predisposed to being lean;

(ii) 7/8 (AT tandem repeat number in exon 18 of the LDLR gene on one chromosome/AT tandem repeat number in exon 18 of the LDLR gene on the other chromosome) indicates the individual is predisposed to being lean;

(iii) 7/10 (AT tandem repeat number in exon 18 of the LDLE gene on one chromosome/AT tandem repeat number in exon 18 of the LDLR gene on the other chromosome) indicates the individual is predisposed to being lean;

(iv) 8/8 (AT tandem repeat number in exon 18 of the LDLR gene on One chromosome/AT tandem repeat number in exon 18 of the LDLR gene on the other chromosome) indicates the individual is predisposed to obesity;

(v) 8/10 (AT tandem repeat number in exon 18 of the LDLR gene on one chromosome/AT tandem repeat number in exon 18 of the LDLR gene on the other chromosome) indicates the individual is predisposed to obesity; and (vi) 10/10 (AT tandem repeat number in exon 18 of the LDLE gene on one chromosome/AT tandem repeat number in exon 18 of the LDLR gene on the other chromosome) indicates the individual is predisposed to obesity.

Support for the determinations of whether an individual is predisposed to being lean or obese is provided in the statistical analysis of the results shown in Examples 2 and 3.

The results of this method also appears to be independent of whether an individual is hypertensive or normotensive. Therefore, the method can be used for hypertensive and normotensive individuals.

Reference may now be made to various preferred embodiments of the invention. Example 1 is a preferred embodiment of the method of the present invention. Examples 2 and 3 are examples of the use of the method and provide supporting evidence for the method. The preferred embodiments are described by way of example only.

BRIEF DESCRIPTION OF THE DRAWINGS

FIG. 1 depicts the sequences of two DNA primers for PCR amplification of the AT tandem repeat region on exon 18 in the LDLR gene.

EXAMPLE 1

Figure 2:
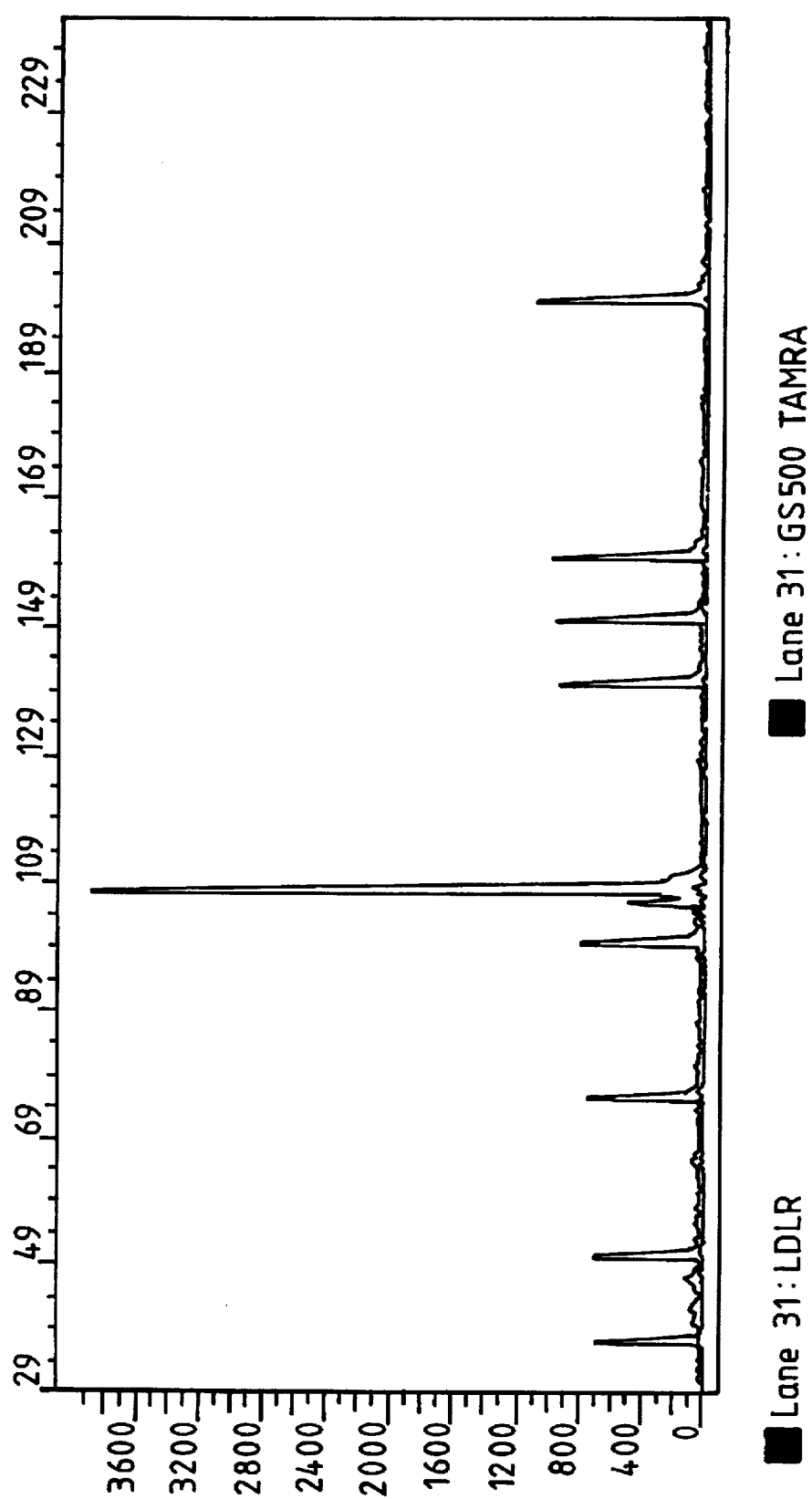
FIG. 2 is a graph depicting Genescan results showing a 106 base pair homozygote for the LDLR AT repeat microsatellite marker. The allele sizes arising for an individual are compared to internal lane standards.

The preferred method of determining whether an individual is predisposed to obesity is described below.

A sample of 20 to 40 mls of blood was extracted from individuals. The sample was centrifuged at 3800 rpm for 10 minutes to separate the blood cells from the serum. The serum was stored at −70° C.

DNA was extracted from isolated blood cells using an adapted salting out method (Miller et al., 1988, *Nucleic Acids Research*, 16, 1215). To 10 mls of blood, NKM (140 mM NaCl, 30 mM KCl, 3 mM $MgCl_2$) was mixed to give a final volume of 25 mL and vigorously shaken for 10 seconds to lyse the cells. After centrifugation at 4800 rpm for 25 minutes, the cell pellet was washed with 25 mL RSB (10 mM Tris-HCl, pH 7.5, 10 mM NaCl, 3 mM $MgCl_2$). The mixture was centrifuged at 4000 rpm with 15 minutes and the pellet was resuspended in 1 ml of RSB followed by the addition of 4 mL of lympholysis buffer (1% SDS, 50 mM Tris-HCl, pH 7.5, 50 mM EDTA, 0.15 mM NaCl) and 0.5 mg/mL of proteinase K. The mixture was incubated overnight at 37° C. in a shaking water bath. After the incubation, 2 mL of a saturated NaCl solution was added and the mixture shaken vigorously for 15 seconds. The proteins were removed by centrifuging for 15 minutes at 2500 rpm. Following the addition of a further 2 mL of saturated NaCl solution to the supernatant and centrifugation at 2500 rpm for minutes, two volumes of absolute ethanol were added to the supernatant and inverted to mix. The clump of precipitated DNA was removed using a disposable inoculation loop and placed in 2 mL of TE buffer and heated at 37° C. for 2 hours to dissolve the DNA.

The LDLR dinucleotiae AT repeat polymorphism was amplified using primers, GZ-7 and GZ-8 (FIG. 1), in the Polymerase Chain Reaction (PCR). The PCR amplification involved final concentrations of 200 μM deoxynucleotides (dATP, dCTP, dGTP and dTTP), 1.75 mM $MgCl_2$, 5 μl of 10 times buffer (500 mM KCl, 100 mM Tris-HCl, pH 9.0, 1% Triton) and 1.2 units of Taq Polymerase together and adding an aliquot to 150 ng purified DNA in a thin walled PCR tube under a biohazard flow hood. The cycling conditions for the PCR amplification were an initial 94° C. denaturing period of four minutes, followed by 35 cycles of 94° C. for 40 seconds; 60° C. for 9 seconds and a final extension period of 72° C. for 120 seconds).

Detection of PCR products involved electrophoresis on a 6% polyacrylamide denaturing gel and analysis using the Applied Biosystems 373 DNA sequencer with Genescan software. Using laser technology to excite the LDLR microsatellite primers, the allele sizes were determined by comparison to fluorescent internal lane standards. Genescan eletrophoretograms and spreadsheets were used to identify genotypes and to determine allele frequencies.

The following results were achievable:

(i) Where only a 106 bp PCR product was detected and identified, it was held that the individual was predisposed to being lean. A 106 bp PCR product represents a 7 tandem repeat in exon 18 of the LDLR gene.

(ii) Where a 106 bp PCR product and a 108 bp PCR product were detected and identified, it was held that the individual was predisposed to being lean. A 108 bp PCR product represents an 8 tandem repeat in exon 18 of the LDLR gene.

(iii) Where a 106 bp PCR product and a 112 bp PCR product were detected and identified, it was held that the individual was predisposed to being lean. A 112 bp PCR product represents a 10 tandem repeat in exon 18 of the LDLR gene.

(iv) Where only a 108 bp PCR product was detected and identified, it was held that the individual was predisposed to obesity.

(v) Where a 108 bp PCR product and a 112 bp PCR product were detected and identified, it was held that the individual was predisposed to obesity.

(vi) Where only a 112 bp PCR product was detected and identified, it was held that individual was predisposed to obesity.

EXAMPLE 2

METHODS:

Subjects

Twenty millilitre blood samples were collected from normotensives for the present cross-sectional association study. Individuals were classified as normotensive if their blood pressure was less than 140/90 mmHg, they were not on hypertensive medication and they had no family history of hypertension, diabetes or heart disease. The population was divided into lean and obese categories on the basis of body mass index (BMI); obese individuals had a BMI of $\geq 26$ kg/m$^2$ and individuals were classified as lean if they had a BMI of <26 kg/m$^2$.

Polymerase chain reaction analysis

DNA was extracted from white blood cells as previously described (Zee, R. Y. L. et al., 1992, supra) and alleles for an LDLR dinucleotide repeat polymorphism were determined using fluorescently labelled primers (FIG. 1) and polymerase chain reaction (PCR) amplification. Polymerase chain reactions were performed as described previously (Zuliani, G. & Hobbs, H. H., 1990, supra), but modified to use a 94° C. initial denaturing step for 3 minutes followed by 35 cycles of denaturation for 40s at 94° C., annealing and extension at 60° C. for 1 minute and a final extension for 2 minutes at 72° C. Polymerase chain reaction products were fractionated on 6% polyacrylamide denaturing gels and alleles were determined by comparison to size standards using an Applied Biosystems DNA sequencer with Genescan software (Perkin-Elmer), as described by Ziegle et al., 1992, *Genomics*, 14, 1026–1031.

Analysis of data

Electrophoretograms and spreadsheets were used to determine the genotypes for each subject tested. The total for each genotype was tabulated and allele frequencies calculated. Differences in frequencies were tested by Chi-squared analysis with two degrees of freedom.

RESULTS

Genotypes for the LDLR dinucleotide tandem repeat were determined for 83 normotensives, 33 of whom were obese and 50 lean. The polymorphic repeat marker has been localised to exon 18 of LDLR. Polymerase chain reaction amplification using the GZ-7 and GZ-8 LDLR oligonucleotide primers detects three DNA fragments, 106, 108, and 112 bp, containing 7, 8, and 10 (TA) repeats, respectively (Zuliani, G. & Hobbs, H. H., 1990, supra). Genotypes were determined after fractionation of amplified, fluorescently labelled PCR products on polyacrylamide denaturing gels and comparison of fragment sizes to labelled standards using Genescan software. The total number of alleles was determined from genotype results and statistical analysis performed (Table 1). Statistical analysis of these results indicated that there was a significant difference between the lean and obese groups of normotensives ($X^2=9.8$; $p=0.008$).

EXAMPLE 3

METHODS

Subjects

Categorising obese subjects required a body mass index of 26 kg/m$^2$ or greater whilst lean subjects required a body mass index less than 26 kg/m$^2$. Individuals were excluded from the study if they had a family history of diabetes or thyroid disease. These conditions were determined by a detailed questionnaire on each of the 92 obese and 158 lean consenting subjects. If individuals satisfied the criteria, 40 mL of blood was extracted from the antecubital fossa of each non-fasting subject and placed in a lithium heparin tube.

Lipid Analysis

Blood being used in the study was transported on ice to the laboratory. The blood sample was centrifuged at 3800 rpm for 10 minutes to separate the blood cells from the serum which was stored at −70° C. The serum was analysed for total cholesterol, high density lipoprotein cholesterol (HDL-cholesterol) and triglyceride.

Cholesterol was analysed on a BM Hitachi 747-200 analyser using the CHOD-PAP enzymatic colorimetric method (Siedel et al., 1983, *Clin. Chem*, 29, 1075). HDL-cholesterol was precipitated with polyethylene glycol. Triglyceride was assayed on the same analyser using the GPO-PAP enzymatic colorimetric method (Wahlefeld, A. W., 1974, Methods of enzymatic analysis, 2nd edition, p 1831. Verlag Chemie Weinheim and Academic Press, Inc. New York).

Genetic Analysis

DNA Extraction

DNA was extracted from isolated blood cells using an adapted salting out method (Miller et al., 1988, supra). To 10 ml of blood, NKM (140 mM NaCl, 30 mM KCl, 3 mM MgCl$_2$) was mixed to give a final volume of 25 mL and vigorously shaken for 10 seconds to lyse the cells. After centrifugation at 4800 rpm for 25 minutes, the cell pellet was washed with 25 mL RSB (10 mM Tris-HCl, pH 7.5, 10 mM NaCl, 3 mM MgCl$_2$). The mixture was centrifuged at 4000 rpm with 15 minutes and the pellet was resuspended in 1 ml of RSB followed by the addition of 4 mL of lympholysis buffer (1% SDS, 50 mM Tris-HCl, pH 7.5, 50 mM EDTA, 0.15 mM NaCl) and 0.5 mg/mL of proteinase K. The mixture was incubated overnight at 37° C. in a shaking water bath. After the incubation, 2 mL of a saturated NaCl solution was added and the mixture shaken vigorously for 15 seconds. The proteins were removed by centrifuging for 15 minutes at 2500 rpm. Following the addition of a further 2 mL of saturated NaCl solution to the supernatant and centrifugation at 2500 rpm for 15 minutes, two volumes of absolute ethanol were added to the supernatant and inverted to mix. The clump of precipitated DNA was removed using a disposable inoculation loop and placed in 2 mL of TE buffer and heated at 37° C. for 2 hours to dissolve the DNA.

PCR amplification

The LDLR dinucleotide AT repeat polymorphism was amplified using primers, GZ-7 and GZ-8 (FIG. 1), in the Polymerase Chain Reaction (PCR). The PCR amplification involved final concentrations of 200 µM deoxynucleotides (dATP, dCTP, dGTP and dTTP), 1.75 mM MgCl$_2$, 5 µl of 10 times buffer (500 mM KCl, 100 mM Tris-HCl, pH 9.0, 1% Triton) and 1.2 units of Taq Polymerase together and adding an aliquot to 150 ng purified DNA in a thin walled PCR tube under a biohazard flow hood. The cycling conditions for the PCR amplification were an initial 94° C. denaturing period of four minutes, followed by 35 cycles of 94° C. for 40 seconds; 60° C. for 9 seconds and a final extension period of 72° C. for 120 seconds).

Detection of PCR products involved electrophoresis on a 6% polyacrylamide denaturing gel and analysis using the Applied Biosystems 373 DNA sequencer with Genescan Software. Using laser technology to excite the LDLR microsatellite primers, the allele sizes were determined by comparison to fluorescent internal lane standards. Genescan cletrophoretograms and spreadsheets were used to identify genotypes and to determine allele frequencies.

Statistical Analysis

Differences in total cholesterol, triglyceride, HDL-cholesterol, LDL-cholesterol and VLDL-cholesterol parameters as compared to body mass index and genotype were determined by one-way analysis of variance (ANOVA). Chi-squared analysis was used to determine any differences between the allele frequencies in the obese and lean subjects.

RESULTS

Figure 3:
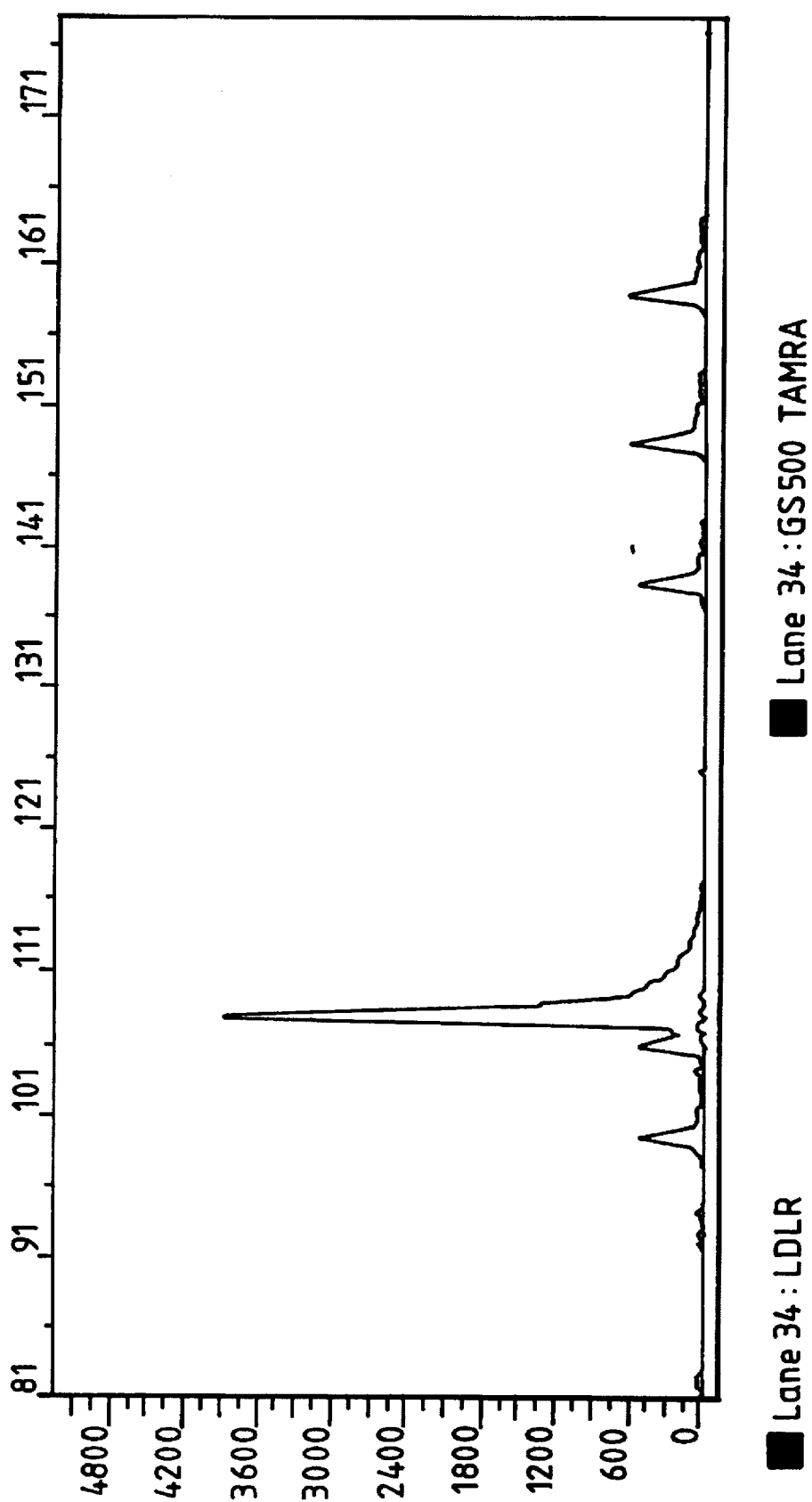
FIG. 3 is also a graph depicting Genescan results showing a 108 bp homozygote for the LDLR AT repeat microsatellite marker.
Figure 4:
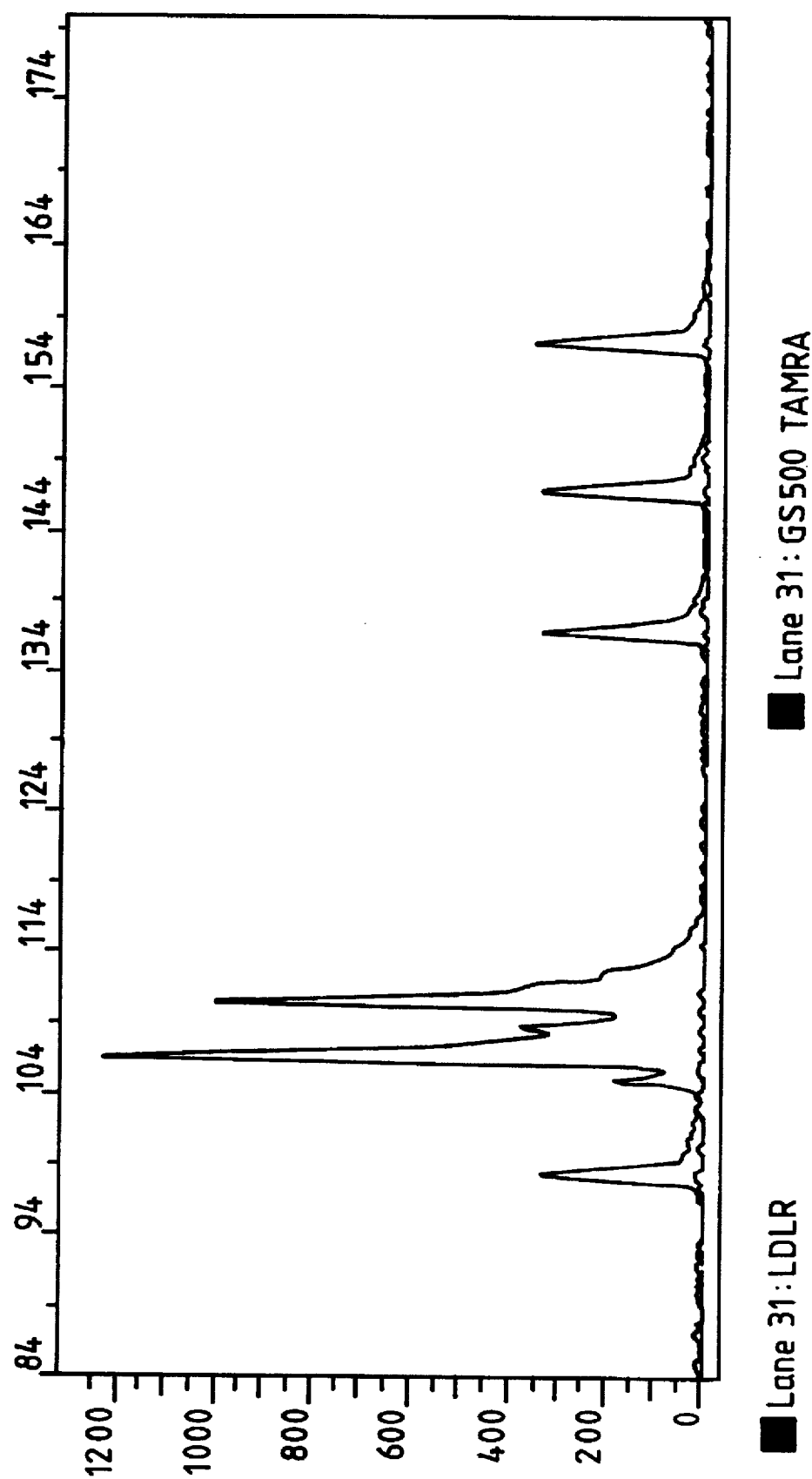
FIG. 4 is another graph depicting Genescan results showing a 108/112 bp heterozygote for the LDLR AT repeat microsatellite marker.
Figure 5:
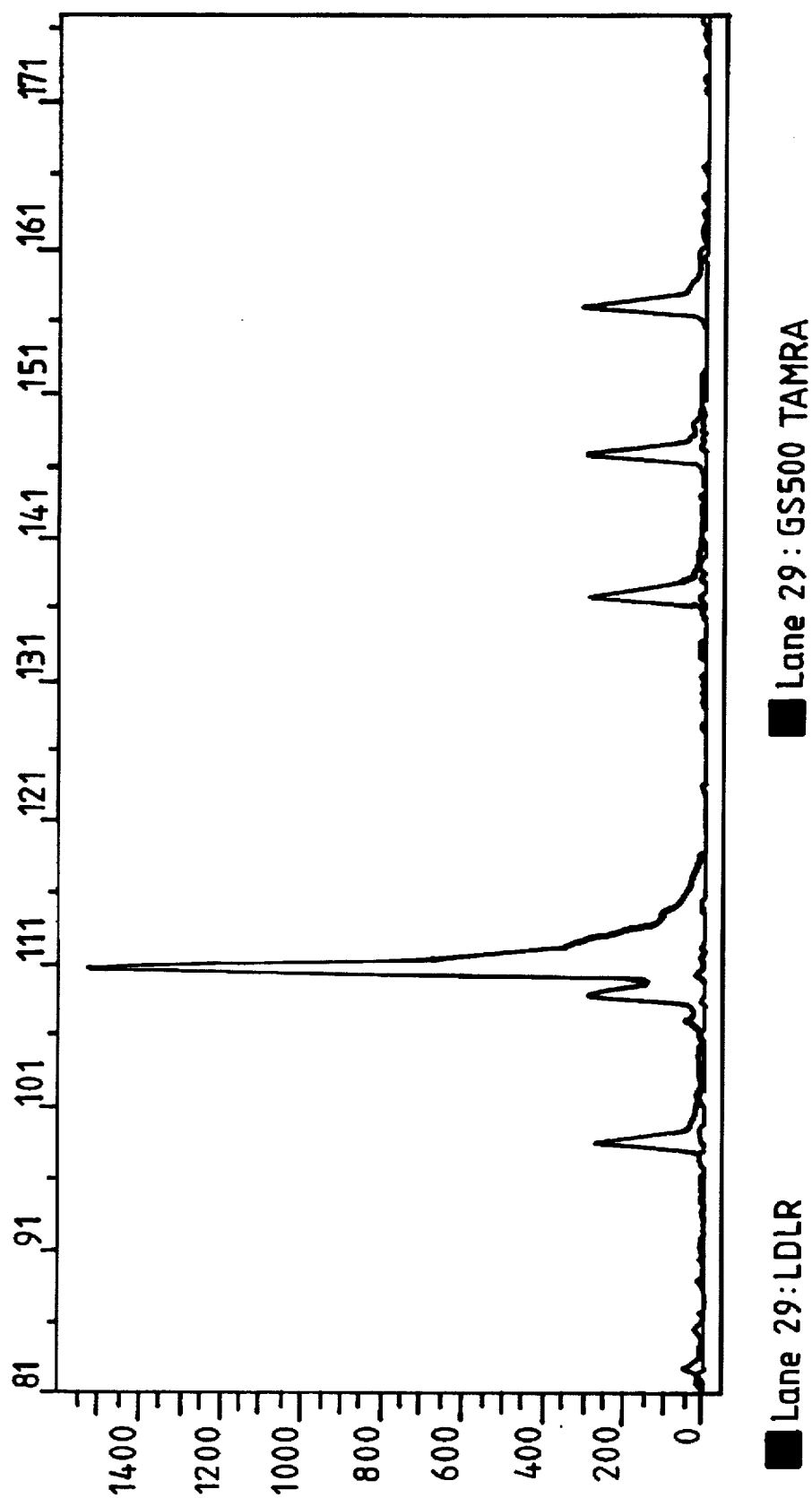
FIG. 5 is yet another graph depicting Genescan results showing a 112/112 bp homozygote for the LDLR AT repeat microsatellite marker.

Following the PCR amplifications of the labelled primers that detect the LDLR dinucleotide AT repeat polymorphism, the ABI DNA sequencer with Genescan software was used to identify fragment sizes. Genescan analysis on the PCR fragments resulted in detection of three alleles of 106 bp, 108 bp and 112 bp. A combination of these alleles results in homozygote genotypes, as shown in FIG. 2 (106/106 bp), FIG. 3 (108 bp), FIG. 5 (112/112 bp) and heterozygote genotypes as shown in FIG. 4 (108/112 pb).

The results of a study on 92 obese subjects with a body mass index equal to or greater than 26 kg/m$^2$ and with 158 lean subjects with a body mass index less than 26 kg/m$^2$ are illustrated in Table 2. Chi-squared analysis on the total allele counts revealed a highly significant difference ($X^2=7.09$, $P=0.0298$) between the lean and obese groups. Furthermore, genotypes were investigated to determine the allele combinations that determine an obese BMI (Table 2). Genotypic analysis indicated that individuals with the 106 bp allele were more likely to be lean than individuals possessing 108 bp or 112 bp alleles.

The results of the one-way anova study comparing the relationship between the plasma lipid concentrations and BMI (Table 3) revealed a significant difference between total cholesterol, triglyceride, HDL-cholesterol, LDL-cholesterol and VLDL-cholesterol concentration. An association can therefore be drawn between obesity and high concentrations for total cholesterol, triglyceride and triglyceride carrying LDL-cholesterol and VLDL-cholesterol lipoproteins whereas obese individuals have a lower HDL-cholesterol concentration.

It has been found that the results of the method of determining whether an individual is predisposed to obesity is independent of hypertension. Of the population tested in this study, 73 were hypertensive (34 lean, 39 obese) and 175 were normotensive (128 lean, 47 obese). When the hypertensives were removed from the analysis and only normotensives tested for significant differences between lean and obese populations, the LDLR microsatellite marker still showed a strongly significant association with obesity ($X^2 6.07$; $P=0.048$). Hence the association of this marker with obesity is independent of hypertension.

DISCUSSION

Results from this study indicated a significant association $X^2=7.09$, $P=0.029$) between the LDLR microsatellite marker located towards the 3' end of the gene and obesity. ANOVA analysis between the lean and obese individuals illustrated that the obese individuals have higher cholesterol, triglyceride and LDL-cholesterol levels which may arise from an impaired LDL receptor regulation and lower HDL-cholesterol levels than lean individuals. The association of LDLR and obesity appears to be related to the importance of the 106 bp allele.

ANOVA analysis on actual BMI values for each genotype revealed the 106 bp allele increases an individuals' chance of being lean. Mean values obtained for BMI indicated that the 106 bp homozygote is associated with a lean BMI. This phenomena appears to be a result of a 106 bp allele dominance.

In this study, a significant association ($X^2=7.09$, $P=0.0298$) between an LDLR microsatellite marker, located towards the 3' end of the gene, and BMI was shown from a cross-sectional analysis study in a general population comprised of obese and lean individuals. These results together with the ANOVA results confirm that there is an association between an LDLR microsatellite and obesity indicating that this gene may play an important role in obesity predisposition.

TABLE 1

Association analysis of a low density lipoprotein receptor dinucleotide repeat polymorphism in obese and lean normotensives

| | | Allele frequencies (bp) | | | Total alleles (bp)* | | |
|---|---|---|---|---|---|---|---|
| NT | NO. | 106 | 108 | 112 | 106 | 108 | 112 |
| Obese | 33 | 0.60 | 0.20 | 0.20 | 40 | 13 | 13 |
| Lean | 50 | 0.78 | 0.17 | 0.05 | 78 | 17 | 5 |

*$x^2 = 9.8$; $P = 0.008$

TABLE 2

Chi-squared anaylsis on allele numbers in lean and obese subjects

| | | Genotype Frequency | | | | | | | | |
|---|---|---|---|---|---|---|---|---|---|---|
| | | 106/ | 106/ | 106/ | 108/ | 108/ | 112/ | Allele Number (bp)* | | |
| | n | 106 | 108 | 112 | 108 | 112 | 112 | 106 | 108 | 112 |
| Obese | 92 | 0.33 | 0.12 | 0.34 | 0.01 | 0.08 | 0.12 | 104 | 20 | 60 |
| Lean | 158 | 0.44 | 0.12 | 0.37 | 0.01 | 0.03 | 0.03 | 216 | 26 | 74 |

*$x^2 = 7.09$; $P = 0.029$

TABLE 3

Results of ANOVA analysis on plasma lipid parameters for the obese and lean subjects

| | BMI | | Statistical Analysis |
|---|---|---|---|
| | Obese | Lean | ANOVA |
| n | 53 | 71 | |
| Total cholesterol | 6.2421 +/− 1.09 | 5.79 +/− 1.02 | 0.0202 |
| Triglyceride | 2.13 +/− 1.11 | 1.70 +/− 1.12 | 0.0351 |
| HDL-cholesterol | 1.38 +/− 0.42 | 1.66 +/− 0.57 | 0.0025 |
| LDL-cholesterol | 3.93 +/− 1.09 | 3.38 +/− 0.97 | 0.0056 |
| VLDL-cholesterol | 0.93 +/− 0.41 | 0.70 +/− 0.49 | 0.0310 |

I claim:

1. A method for detecting whether an individual is predisposed to obesity, comprising the steps of:
    i) obtaining a sample containing human genomic DNA from said individual,
    ii) detecting whether genomic DNA in said sample has a 7 AT tandem repeat in exon 18 of the low density lipoprotein receptor gene on one or both chromosomes containing said gene, and
    iii) correlating the absence of the 7 AT tandem repeat on said chromosome or chromosomes with a predisposition to obesity in said individual.

2. A method as claimed in claim 1 wherein the presence of the 7 AT tandem repeat indicates said individual is predisposed to being lean.

3. A method for detecting whether an individual is predisposed to obesity, comprising the steps of:
    i) obtaining a sample of blood containing human genomic DNA from said individual,
    ii) detecting whether said genomic DNA in said sample has a 7 AT tandem repeat in exon 18 of the low density lipoprotein receptor gene on one or both chromosomes containing said gene by PCR amplification using SEQ ID NO:1 and/or SEQ ID NO:2 as primers and identifying one or more PCR products by electrophoretic separation, and
    iii) correlating the presence of a 106 bp PCR product with a predisposition to leanness in said individual, and correlating the absence of the 106 bp PCR product with a predisposition to obesity in said individual, wherein the presence of the 106 bp PCR product is correlated with the presence of the 7 AT tandem repeat.

4. A method for detecting whether an individual is predisposed to obesity, comprising the steps of:
    i) obtaining a sample containing human genomic DNA from said individual,
    ii) detecting whether said genomic DNA in said sample has a 7, 8, and/or 10 AT tandem repeat in exon 18 of the low density lipoprotein receptor gene on one or both chromosomes containing said gene, and
    iii) correlating:
        (a) the presence of the 7 AT tandem repeat on both of the chromosomes with a predisposition to leanness in said individual;
        (b) the presence of the 7 AT tandem repeat on one of the chromosomes and the 8 AT tandem repeat on the other chromosome with a predisposition to leanness in said individual;
        (c) the presence of the 7 AT tandem repeat on one of the chromosomes and the 10 AT tandem repeat on the other chromosome with a predisposition to leanness in said individual;
        (d) the presence of the 8 AT tandem repeat on both of the chromosomes with a predisposition to obesity in said individual;

(e) the presence of the 8 AT tandem repeat on one of the chromosomes and the 10 AT tandem repeat on the other chromosome with a predisposition to obesity in said individual; or (f) the presence of the 10 AT tandem repeat on both of the chromosomes with a predisposition to obesity in said individual.

5. A method for detecting whether an individual is predisposed to obesity, comprising the steps of:

i) obtaining a sample of blood containing human genomic DNA from said individual, ii) detecting whether said genomic DNA in said sample has a 7, 8, and/or 10 AT tandem repeat in exon 18 of the low density lipoprotein receptor gene on one or both chromosomes containing said gene by PCR amplification using SEQ ID NO:1 and/or SEQ ID NO:2 as primers and identifying one or more PCR products by electrophoretic separation, and iii) correlating:
(a) the presence of a 106 bp PCR product with a predisposition to leanness in said individual;

(b) the presence of only the 106 bp PCR product and a 108 bp PCR product with a predisposition to leanness in said individual;

(c) the presence of the 106 bp PCR product and a 112 bp PCR product with a predisposition to leanness in said individual;

(d) the presence of only a 108 bp PCR product with a predisposition to obesity in said individual;

(e) the presence of the 108 bp PCR product and the 112 bp PCR product with a predisposition to obesity in said individual; or (f) the presence of only the 112 bp PCR product with a predisposition to obesity in said individual, wherein the presence of the 106 bp PCR product, the 108 bp PCR product, and the 112 bp PCR product are correlated with the presence of the 7 AT tandem repeat, the 8 AT tandem repeat, and the 10 AT tandem repeat, respectively.

* * * * *